US007903331B2

(12) United States Patent
Cech

(10) Patent No.: US 7,903,331 B2
(45) Date of Patent: *Mar. 8, 2011

(54) FLEXIBLE POSITIONER AND OPHTHALMIC MICROSCOPE INCORPORATING THE SAME

(75) Inventor: Steven D. Cech, Aurora, OH (US)

(73) Assignee: Volk Optical, Inc., Mentor, OH (US)

( * ) Notice: Subject to any disclaimer, the term of this patent is extended or adjusted under 35 U.S.C. 154(b) by 718 days.

This patent is subject to a terminal disclaimer.

(21) Appl. No.: 11/828,432

(22) Filed: Jul. 26, 2007

(65) Prior Publication Data

US 2008/0013188 A1     Jan. 17, 2008

Related U.S. Application Data

(60) Provisional application No. 60/820,892, filed on Jul. 31, 2006, provisional application No. 60/821,054, filed on Aug. 1, 2006, provisional application No. 60/864,042, filed on Nov. 2, 2006.

(51) Int. Cl.
*G02B 21/00* (2006.01)
(52) U.S. Cl. .................... 359/381; 248/276.1
(58) Field of Classification Search .......... 359/368, 359/376–378, 506, 381; 248/276.1
See application file for complete search history.

(56) References Cited

U.S. PATENT DOCUMENTS

| 3,200,304 | A | 8/1965 | Atkins et al. |
| 3,254,313 | A | 5/1966 | Atkins et al. |
| 3,715,540 | A | 2/1973 | Larson |
| 4,190,322 | A | 2/1980 | Wortley |
| 4,807,989 | A | 2/1989 | Nagano et al. |
| 4,885,667 | A | 12/1989 | Selden |
| 4,887,193 | A | 12/1989 | Dieckmann |
| 4,963,903 | A | 10/1990 | Cane |
| 5,339,799 | A | 8/1994 | Kami et al. |

(Continued)

FOREIGN PATENT DOCUMENTS

WO    WO 91/15150    10/1991

OTHER PUBLICATIONS

PCT International Search Report for International application No. PCT/US2007/074807 dated Jan. 7, 2008.

*Primary Examiner* — Alessandro Amari
(74) *Attorney, Agent, or Firm* — Dinsmore & Shohl LLP

(57) ABSTRACT

In accordance with one embodiment of the present invention, a microscope is provided comprising a microscope assembly and a lens positioner. The lens positioner comprises a tension control assembly, an adjustable lens extension assembly, and a tensile cord coupling the tension control assembly to the adjustable lens extension assembly. The tension control assembly is configured to control the degree of tension in the tensile cord. The adjustable lens extension assembly comprises a flexible linkage subassembly and a lens support subassembly. The flexible linkage subassembly comprises a proximal end and a distal end and is configured such that the distal end is movable relative to the proximal end through a plurality of degrees of freedom of movement. The lens support subassembly is secured to the distal end of the flexible linkage subassembly. The flexible linkage subassembly is further configured such that the ease at which its distal end moves relative to its proximal end is a function of the degree of tension in the tensile cord, as controlled by the tension control assembly.

20 Claims, 7 Drawing Sheets

U.S. PATENT DOCUMENTS

| | | |
|---|---|---|
| 5,495,286 A | 2/1996 | Adair |
| 5,526,074 A | 6/1996 | Volk |
| 5,793,469 A | 8/1998 | Feiertag et al. |
| 5,793,524 A | 8/1998 | Luloh |
| 5,810,306 A | 9/1998 | Hung et al. |
| 5,847,883 A | 12/1998 | Rispoli, Sr. |
| 5,899,425 A * | 5/1999 | Corey, Jr. et al. .......... 248/276.1 |
| 6,439,721 B1 | 8/2002 | Reiner et al. |
| 6,733,128 B2 | 5/2004 | Kirchhuebel |
| 6,788,455 B2 | 9/2004 | Kirchhuebel et al. |
| 6,916,000 B2 | 7/2005 | Weiss |
| 6,967,774 B2 | 11/2005 | Kirchhuebel et al. |
| 7,002,737 B1 | 2/2006 | Akiyama et al. |
| 7,092,152 B2 | 8/2006 | Kirchhuebel |
| 2004/0218266 A1 | 11/2004 | Kirchhuebel et al. |
| 2008/0239524 A1 * | 10/2008 | Cech et al. .................... 359/824 |

* cited by examiner

Fig. 7
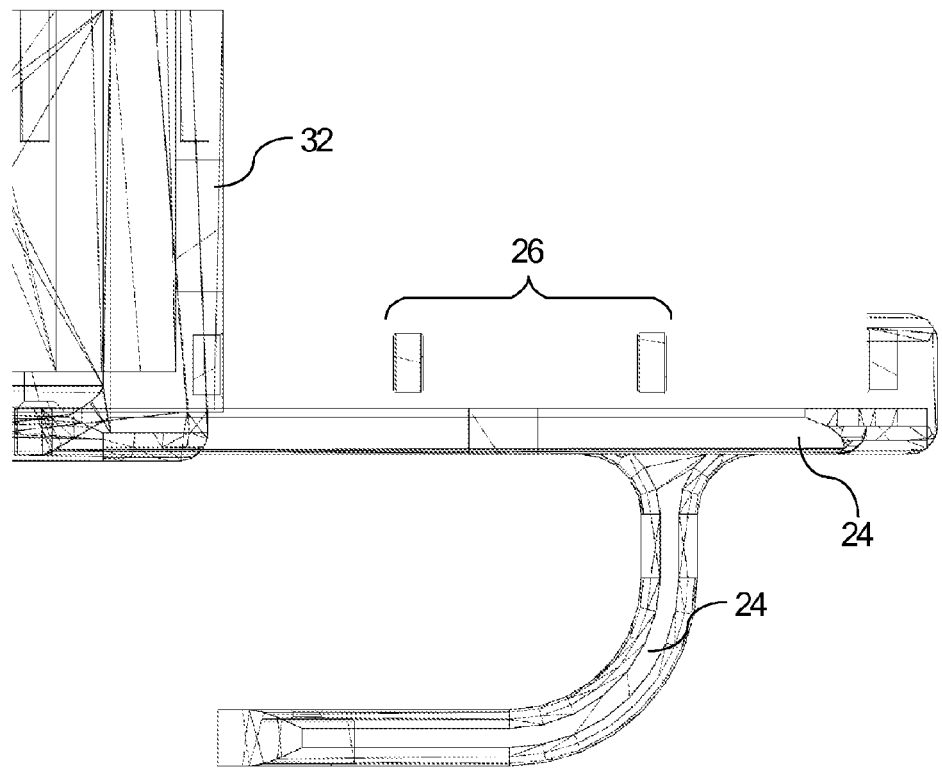
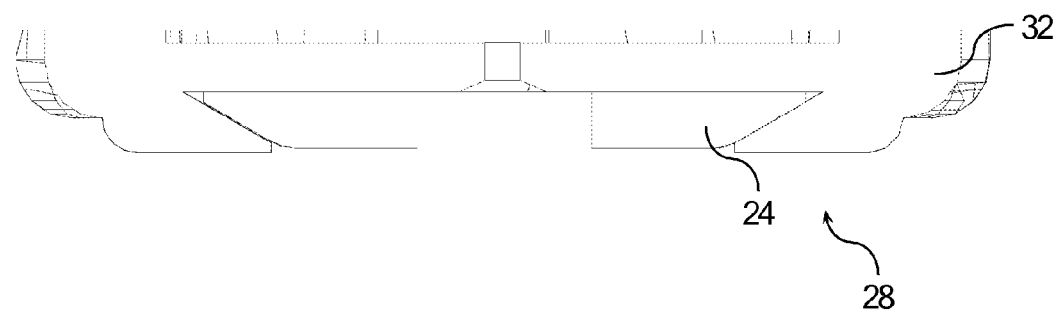
Fig. 8

US 7,903,331 B2

FLEXIBLE POSITIONER AND OPHTHALMIC MICROSCOPE INCORPORATING THE SAME

CROSS-REFERENCE TO RELATED APPLICATIONS

This application claims the benefit of U.S. Provisional Application Ser. Nos. 60/820,892, filed Jul. 31, 2006, 60/821,054, filed Aug. 1, 2006, and 60/864,042, filed Nov. 2, 2006.

BACKGROUND

The present invention relates to lens positioning in ophthalmic microscopy, or other types of microscopy. The present invention also relates more generally to controllable object positioning, without regard to whether the positioner or its individual components are used in microscopy.

BRIEF SUMMARY

In accordance with one embodiment of the present invention, a microscope is provided comprising a microscope assembly and a lens positioner. The lens positioner comprises a tension control assembly, an adjustable lens extension assembly, and a tensile cord coupling the tension control assembly to the adjustable lens extension assembly. The tension control assembly is configured to control the degree of tension in the tensile cord. The adjustable lens extension assembly comprises a flexible linkage subassembly and a lens support subassembly. The flexible linkage subassembly comprises a proximal end and a distal end and is configured such that the distal end is movable relative to the proximal end through a plurality of degrees of freedom of movement. The lens support subassembly is secured to the distal end of the flexible linkage subassembly. The flexible linkage subassembly is further configured such that the ease at which its distal end moves relative to its proximal end is a function of the degree of tension in the tensile cord, as controlled by the tension control assembly.

In accordance with another embodiment of the present invention, a positioner is provided comprising a tension control assembly, an adjustable extension assembly, and a tensile cord coupling the tension control assembly to the adjustable extension assembly.

BRIEF DESCRIPTION OF THE SEVERAL VIEWS OF THE DRAWINGS

The following detailed description of specific embodiments of the present invention can be best understood when read in conjunction with the following drawings, where like structure is indicated with like reference numerals and in which:

FIGS. 7 and 8, where FIG. 7 is an exploded view and FIG. 8 is taken in cross section, illustrate portions of a tension control assembly according to the present invention.

DETAILED DESCRIPTION

Figure 1:
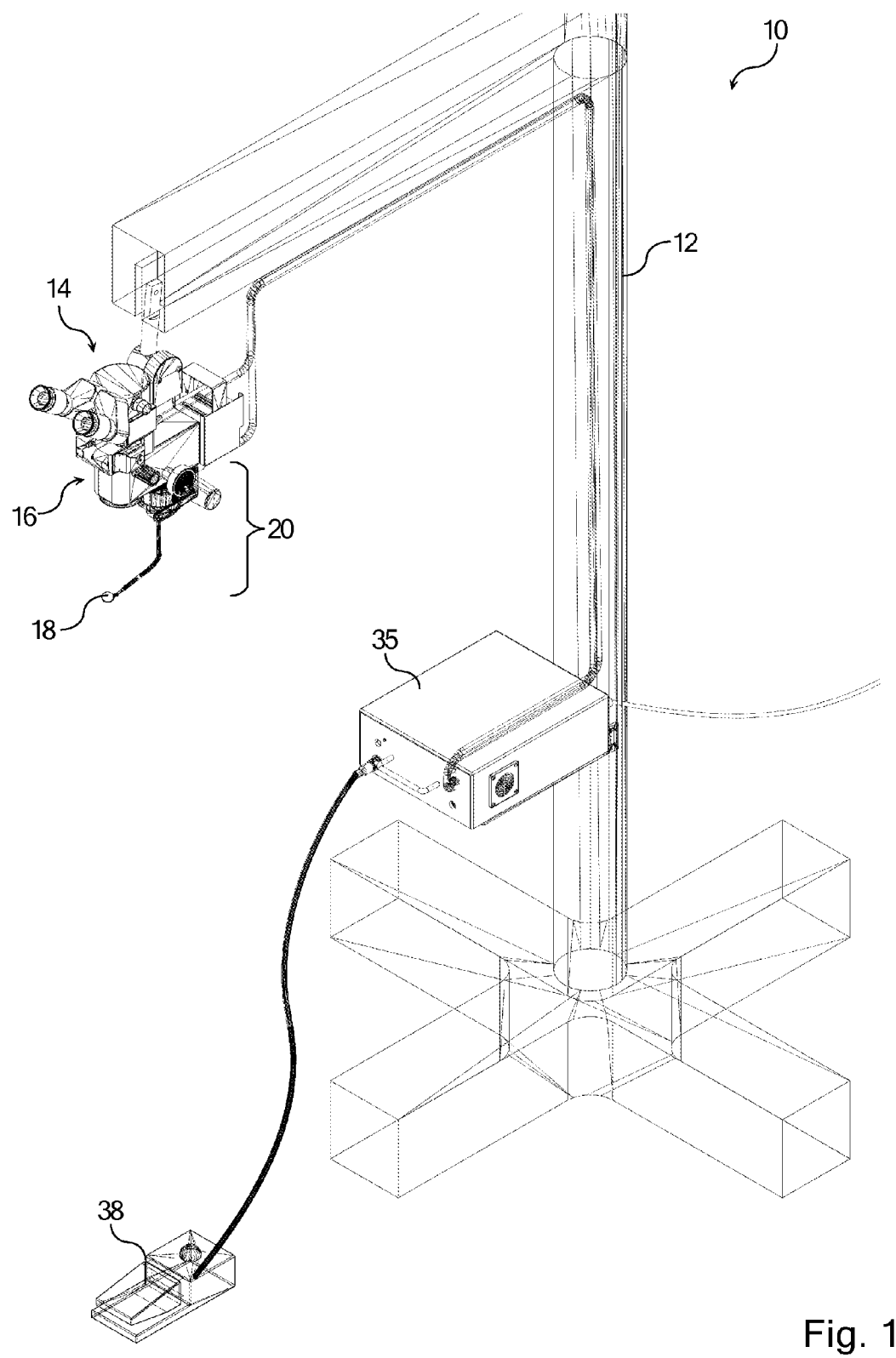
FIG. 1 is an illustration of an ophthalmic microscope incorporating a lens positioner according to one embodiment of the present invention.
Figure 2:
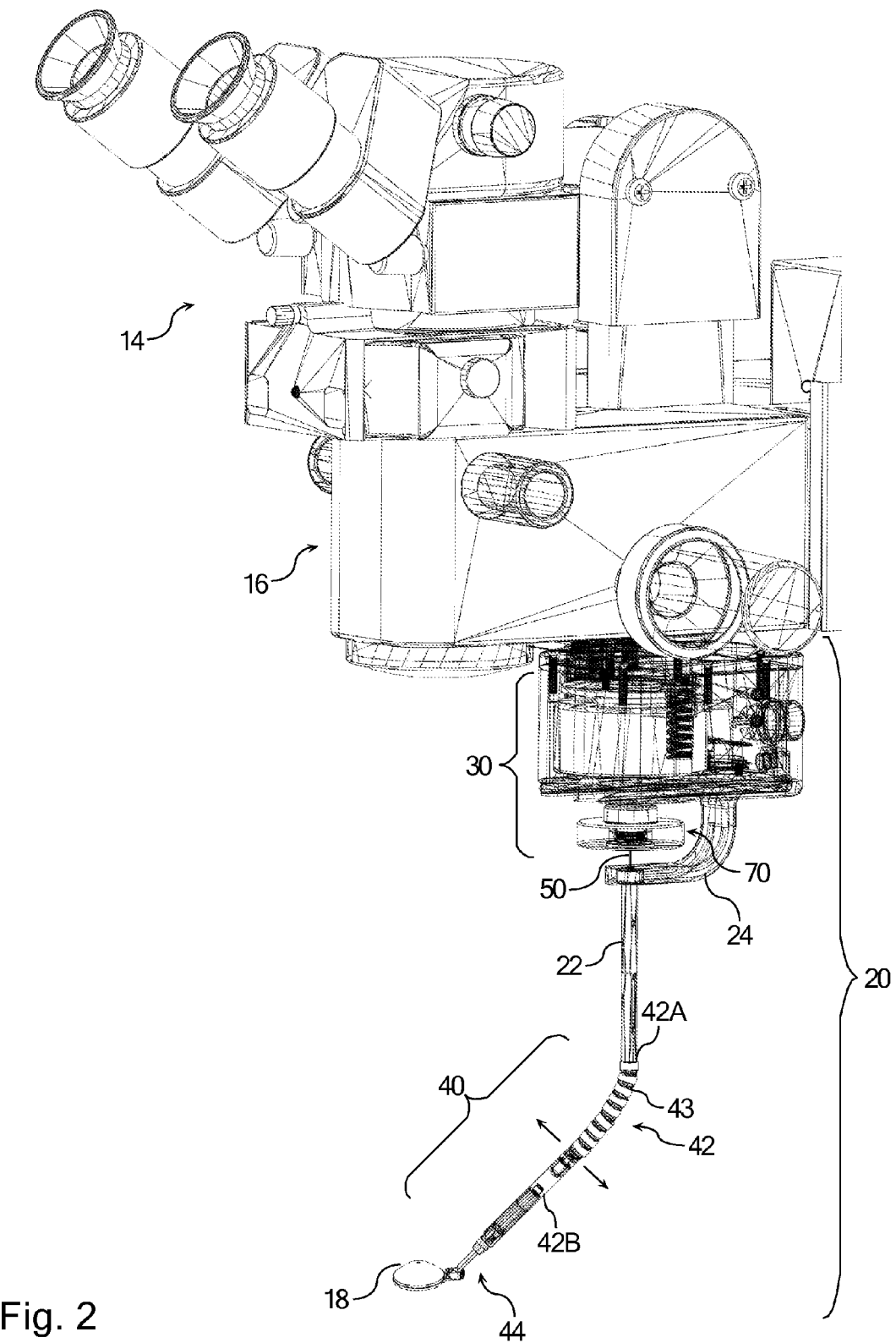
FIG. 2 is a magnified view of the microscope assembly and lens positioner illustrated in FIG. 1.

Referring initially to FIGS. 1 and 2, the various concepts of particular embodiments of the present invention can be illustrated in the context of an ophthalmic microscope 10 mounted to a microscope stand 12. More specifically, as will be appreciated by those familiar with the art of ophthalmic microscopy, the illustrated microscope is particularly well configured for non-contact, high magnification, indirect imaging during vitreoretinal procedures and, to this end, includes a microscope assembly 14, wide-angle viewing optics 16, such as a Reinverting Operating Lens System® (ROLS®), and a wide angle lens 18. Generally, the wide-angle viewing optics 16 and wide angle lens 18 cooperate to present the fundus image and surgical instrumentation in the eye in an upright and correctly oriented position, and enhances left/right eye image fusion, high efficiency light transmission and optical transparency for improved views of the interior of the eye, although the concepts of the present invention are not limited to any particular microscope, viewing optics, or lens configuration.

To operate the ophthalmic microscope 10 illustrated in FIGS. 1 and 2, it is typically necessary to manually position and reposition the wide angle lens 18. To this end, the ophthalmic microscope 10 is provided with a lens positioner 20. In the illustrated embodiment, the lens positioner 20 comprises a tension control assembly 30, an adjustable lens extension assembly 40, and a tensile cord 50 coupling the tension control assembly 30 to the adjustable lens extension assembly 40, which comprises a flexible linkage subassembly 42 and a lens support subassembly 44. The flexible linkage subassembly 42 comprises a proximal end 42A and a distal end 42B and is configured such that the distal end 42B, i.e., the end to which the lens support subassembly 44 is secured, is movable relative to the proximal end 42A through a plurality of degrees of freedom of movement. This movement is partially illustrated by the directional arrows in FIG. 2.

The flexible linkage subassembly 42 is further configured such that the ease at which its distal end 42B moves relative to its proximal end 42A is a function of the degree of tension in the tensile cord 50. This degree of tension can be controlled on a selective basis by the tension control assembly 30. Accordingly, in operation, the tension control assembly 30 controls the degree of tension in the tensile cord 50 to permit or inhibit movement of the distal end 42B of the flexible linkage subassembly 42 relative to the proximal end 42A of the flexible linkage subassembly 42 on a selective basis, permitting adjustment and readjustment of the position of the wide angle lens 18 through multiple degrees of freedom.

Figure 3:
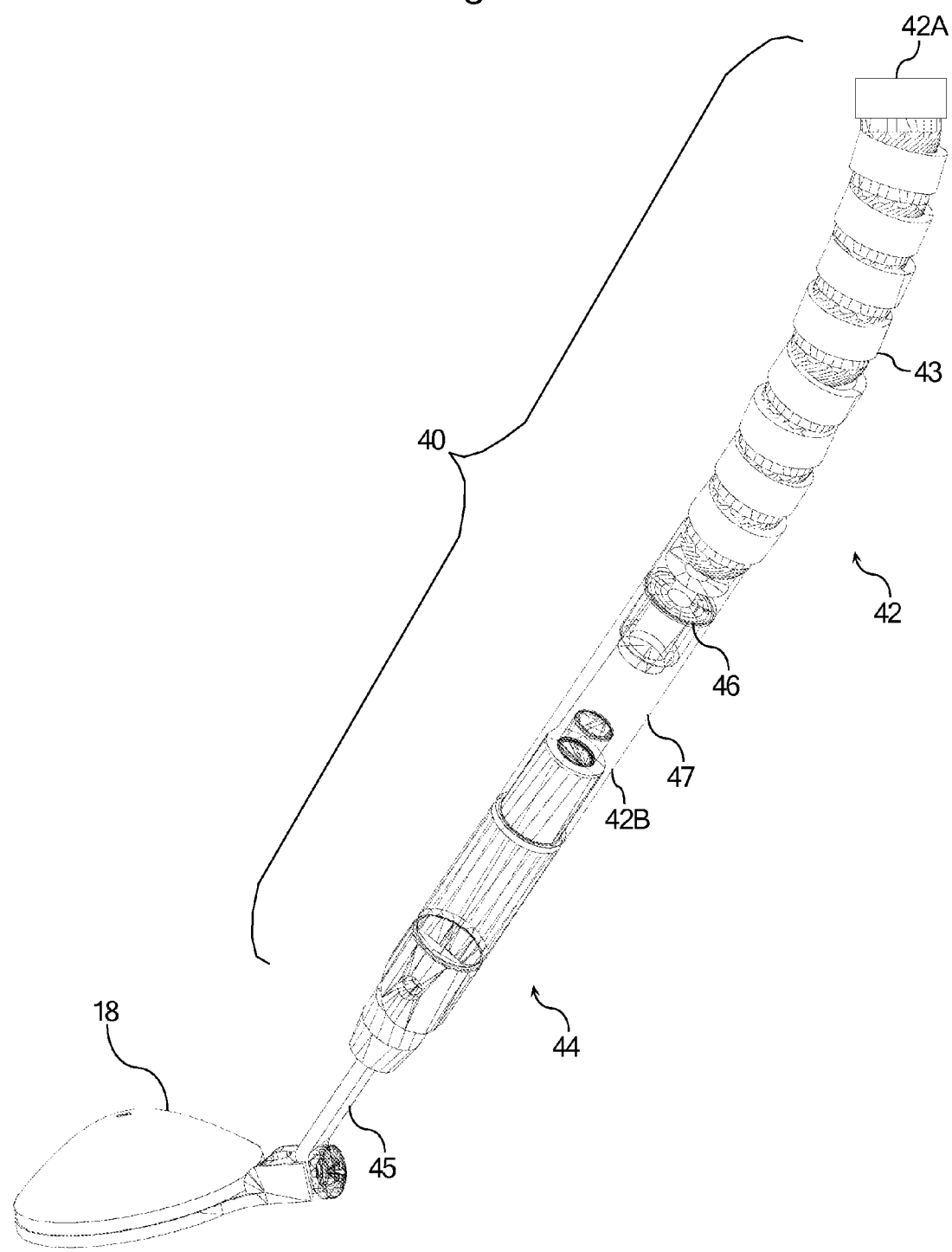
FIG. 3 is an illustration of an adjustable lens extension assembly in accordance with one embodiment of the present invention.
Figure 4:
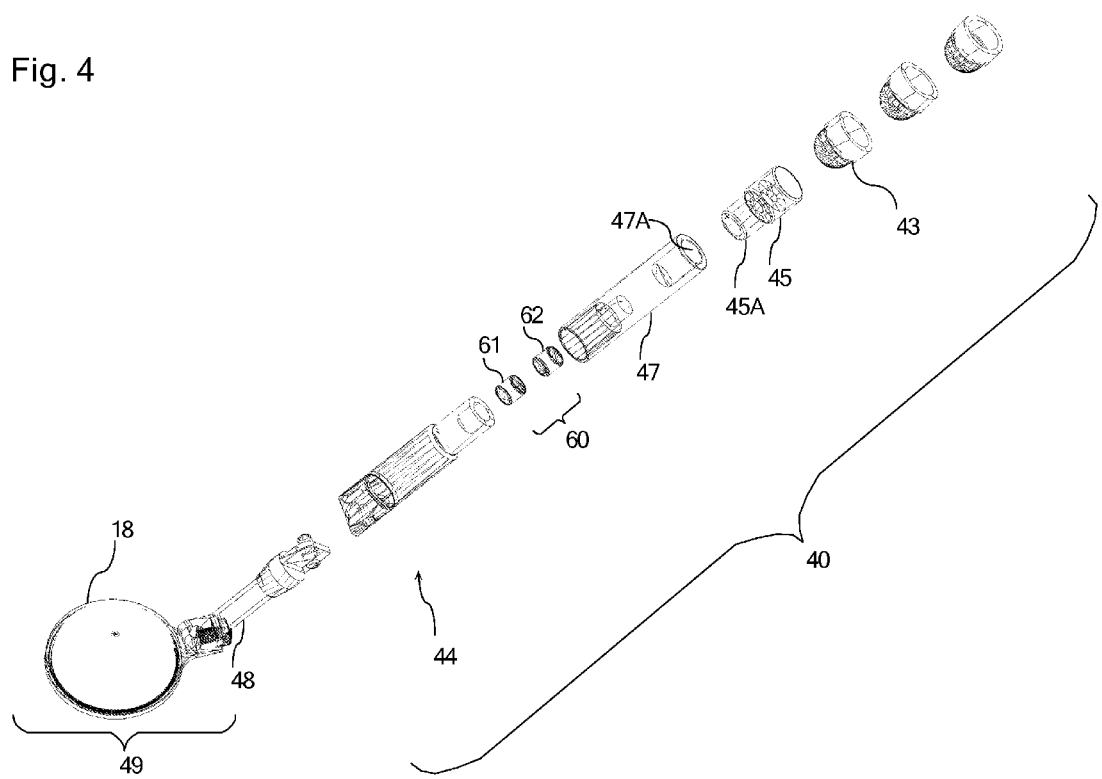
FIG. 4 is an exploded illustration of the adjustable lens extension assembly of FIG. 3.

A more detailed illustration of an adjustable lens extension assembly 40 according to one embodiment of the present invention is presented in FIGS. 3 and 4. As is noted above, the adjustable lens extension assembly 40 comprises the flexible linkage subassembly 42 and the lens support subassembly 44. The flexible linkage subassembly comprises a plurality of ball-and-socket type links 43, each comprising a central bore sufficient to accommodate passage of the tensile cord there through. Collectively, this series of ball-and-socket links exhibit a mechanical preference for immobility as the degree of tension in the tensile cord increases. Stated differently, when the tensile cord 50 is in a relatively relaxed but not unduly loose state, the distal end 42B of the flexible linkage subassembly 42 can be easily adjusted relative to the proximal end 42A of the flexible linkage subassembly 42. In contrast, when the tensile cord 50 is in a relatively taut state, it becomes more difficult to adjust the position of the distal end 42B of the flexible linkage subassembly 42. Typically, the degree of tension in the relatively taut state will be sufficient to lock the distal end 42 in a set position under normal microscope operating conditions. If readjustment is needed, the degree of tension in the tensile cord 50 can be relaxed to permit convenient movement of the distal end 42. For example, and not by way of limitation, it is contemplated that it will typically be sufficient to apply a load of up to about 100 lbs, or higher, to the tensile cord 50 to lock the position of the distal end 42 of the flexible linkage subassembly 40. In the relatively relaxed state, the load on the tensile cord 50 may drop as low as 5 lbs, or lower.

The lens positioner 20 may further comprise a coupling linkage 22 that can be used to indirectly couple the adjustable lens extension assembly 40 to a mechanical stop 24 provided by the tension control assembly 30. Referring to FIGS. 7 and 8, it is noted that the mechanical stop 24 can be secured to the remainder of the tension control assembly 30 via a magnetic coupling in the form of a pair of magnets 26, each of which can be secured within respective recesses formed in mating components of the tension control assembly 30, as is illustrated in detail in FIG. 7. The degree of securement attributable to the magnetic coupling is such that the mechanical stop 24 may be manually disengaged from the remainder of the tension control assembly 30 to facilitate maintenance, cleaning, or sterilization. As is illustrated in FIG. 8, the engagement of the mechanical stop to the remainder of the tension control assembly 30 can be enhanced by providing a sliding dovetail engagement, illustrated generally at 28. Of course, it is contemplated that any of a variety of conventional or yet to be developed hardware for releasably securing the mechanical stop 24 to the remainder of the tension control assembly 30 would fall within the scope of the present invention.

Referring further to FIGS. 3 and 4, it is noted that the flexible linkage subassembly 42 comprises a cord accommodating passage that extends from the proximal end 42A of the flexible linkage subassembly 40 to the distal end 42B of the flexible linkage subassembly 42. Further, the flexible linkage subassembly 42 comprises a cord anchor 46 at its distal end 42B, which anchor 46 is used to secure one end of the tensile cord 50. For the purposes of describing and defining the present invention, it is noted that the term "cord" is intended to refer broadly to any longitudinally extending tensile member, e.g., cable, wire, strand, linkage assembly, etc.

For the purposes of describing and defining the present invention, it is noted that a variety of structures may be employed in constructing the flexible linkage subassembly 42 including, but not limited to, the ball-and-socket type links described above or any other types of links or hardware that can be used to create a flexible extension that can be "locked" or "unlocked" in response to variations in tension applied to a tensile cord. For example, it is contemplated that any the flexible linkage subassembly incorporating friction-based locking hardware would fall within the scope of the present invention.

Referring further to FIG. 4, the flexible linkage subassembly 42 may comprise an adjustment arm 45 configured to permit selective adjustment of the tension in the tensile cord by reducing or extending the length of the flexible linkage subassembly 42. More specifically, in the illustrated embodiment, the adjustment arm 45 comprises an external threaded surface 45A that engages a complementary threaded bore 47A in sleeve 47. Accordingly, the degree of tension in the tensile cord 50 can be adjusted via the threaded engagement by rotating the adjustment arm 45 to alter the length of the flexible linkage subassembly 42, with longer lengths associated with increased tension and shorter lengths associated with less tension. The aforementioned selective adjustment of tension in the tensile cord will typically be employed to ensure sufficient degrees of tension in the taut and relaxed tensile states of the tensile cord 50, permitting the tension control assembly 30 and flexible linkage subassembly 42 to operate properly. The thrust bearing subassembly 70, described in detail below with reference to FIG. 6 may alternatively be employed to provide this type of adjustment.

FIGS. 3 and 4 also illustrate the lens support subassembly 44 in detail. In the illustrated embodiment, the lens support subassembly 44 is secured to the distal end 42B of the flexible linkage subassembly 42 via a magnetic coupling 60 comprising first and second magnets 61, 62, which are mounted within respective recesses formed in the distal end 42B of the flexible linkage subassembly 42 and a corresponding end of the lens support subassembly 44. Preferably, the degree of securement attributable to the magnetic coupling is such that the lens support subassembly 44 can be manually removed from the flexible linkage subassembly 42 to facilitate maintenance, cleaning, or sterilization, or to allow for convenient interchange of different lens support subassemblies 44 with the flexible linkage subassembly 42. Of course, it is contemplated that any of a variety of conventional or yet to be developed hardware for releasably securing the lens support subassembly 44 to the distal end 42B of the flexible linkage subassembly 42 would fall within the scope of the present invention.

The lens support subassembly 44 further comprises a hinged lens arm 48 and the adjustable lens extension assembly 40 further comprises a lens housing subassembly 49 secured to the lens support subassembly 44 via the hinged lens arm 48. The hinged lens arm provides a further point of control in adjusting the position of the wide angle lens 18.

Figure 5:
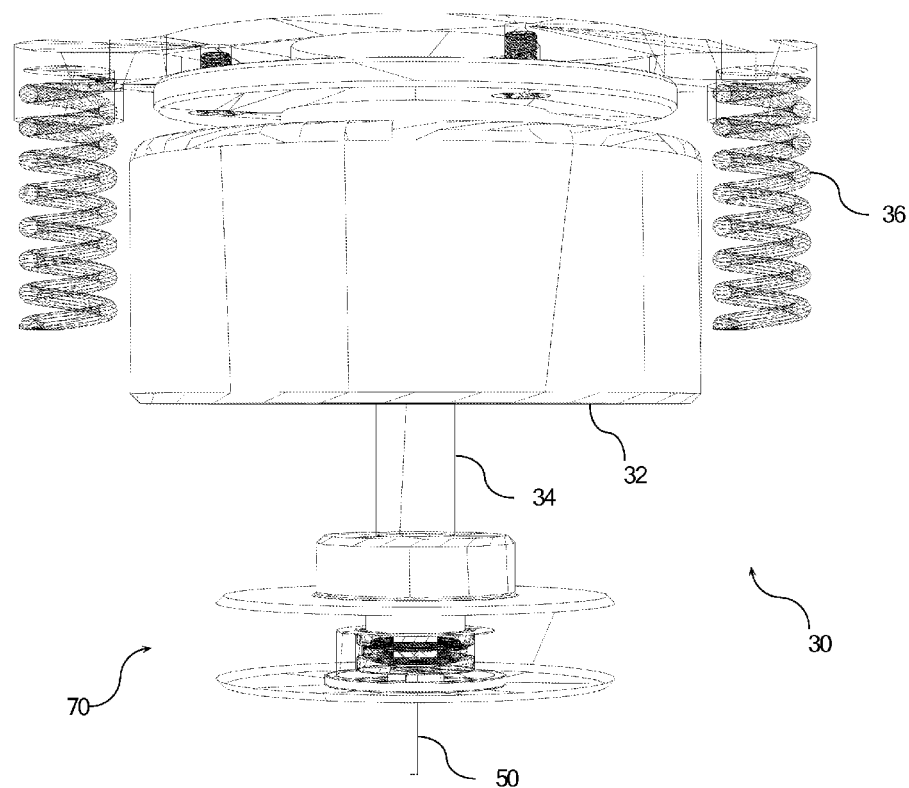
FIG. 5 is a perspective view of particular components of a tension control assembly according to the present invention.

Referring to FIG. 5, the tension control assembly 30 may comprise a solenoid actuated tension control mechanism 32 coupled to the tensile cord 50 via a thrust bearing subassembly 70 that is secured to opposing ends of the tensile cord 50 and a solenoid plunger 34 of the tension control assembly 30. The solenoid actuated tension control mechanism 32 places the tensile cord 50 in a relatively taut state when its solenoid is deactivated and in a relatively relaxed state when its solenoid is activated. Further, the tension control assembly 30 comprises a spring-loaded tension control mechanism (see springs 36) that places the tensile cord 50 in a relatively taut state when the tension control assembly is at rest. Although FIG. 5 specifically illustrates a solenoid actuated control mechanism 32, it is contemplated that a variety of other types of actuation mechanisms may be employed in the tension control assembly 30 of the present invention. For example, and not by way of limitation, it is contemplated that motor driven actuators, e.g., screw-based linear actuators, and solid state actuators, e.g., piezoelectric or magnetortrictive actuators, may be employed without departing from the scope of the present invention.

Returning to FIG. 1, the tension control assembly 30 further comprises a controller 35 and a foot-activated switch 38 coupled to the controller 35. The controller 35, which includes a suitable power supply, and the foot-activated switch 38 cooperate to control actuation of the solenoid actuated tension control mechanism 32. Alternatively, the tension control assembly 30 may comprise touch-sensitive switching circuitry coupled to the controller 35 to enable selective actuation of the solenoid actuated tension control mechanism 32. Generally, the touch-sensitive switching circuitry and the controller 35 can be configured to provide an electrical switching response to human contact with selected portions of the flexible linkage subassembly 42, the lens support subassembly 44, the lens housing subassembly 49, or combinations thereof.

More specifically, the touch-sensitive switching circuitry comprises one or more electrical conductors that are conductively coupled to one or more electrically conductive touch sensitive areas of the adjustable lens extension assembly 40. In this manner, touch activation of the tension control assembly 30 will allow a user to adjust the position of the wide angle lens 18 without having to operate a foot pedal or any other peripheral switching device. Typically, when the touch sensitive control area is untouched, the positioner tension control assembly will lie in a "locked" state. Once a user touches a touch sensitive control area of the flexible linkage subassembly 42, the lens support subassembly 44, or the lens housing subassembly 49, the switching circuitry detects the electrical signal provided by the user's touch and activates the tension control mechanism 32, which mechanically unlocks the adjustable lens extension assembly 40, as described above. As the user grips the touch sensitive control area, the user is free to naturally move lens 18 to a desired position. Once the user has moved lens 18 to the desired location and has removed his or her grip from the touch sensitive control area, the switching circuitry detects the removal of the electrical signal provided by the user's touch and deactivates the tension control mechanism 32, thereby locking adjustable lens extension assembly 40 and the lens 18 in the desired location.

As will be appreciated by those familiar with touch sensitive switching circuitry, examples of which are discussed in U.S. Pat. No. 3,200,304 to Atkins; U.S. Pat. No. 3,254,313 to Atkins; and U.S. Pat. No. 3,715,540 to Larson, the relevant portions of which are incorporated herein by reference, the touch sensitive control area should be configured to provide an electrical signal in response to a user's touch. The touch sensitive control area and accompanying circuitry may employ technology that includes, but is not limited to, capacitance, resistance, frequency, and/or voltage detection to change the state of the switching circuitry.

Figure 6:
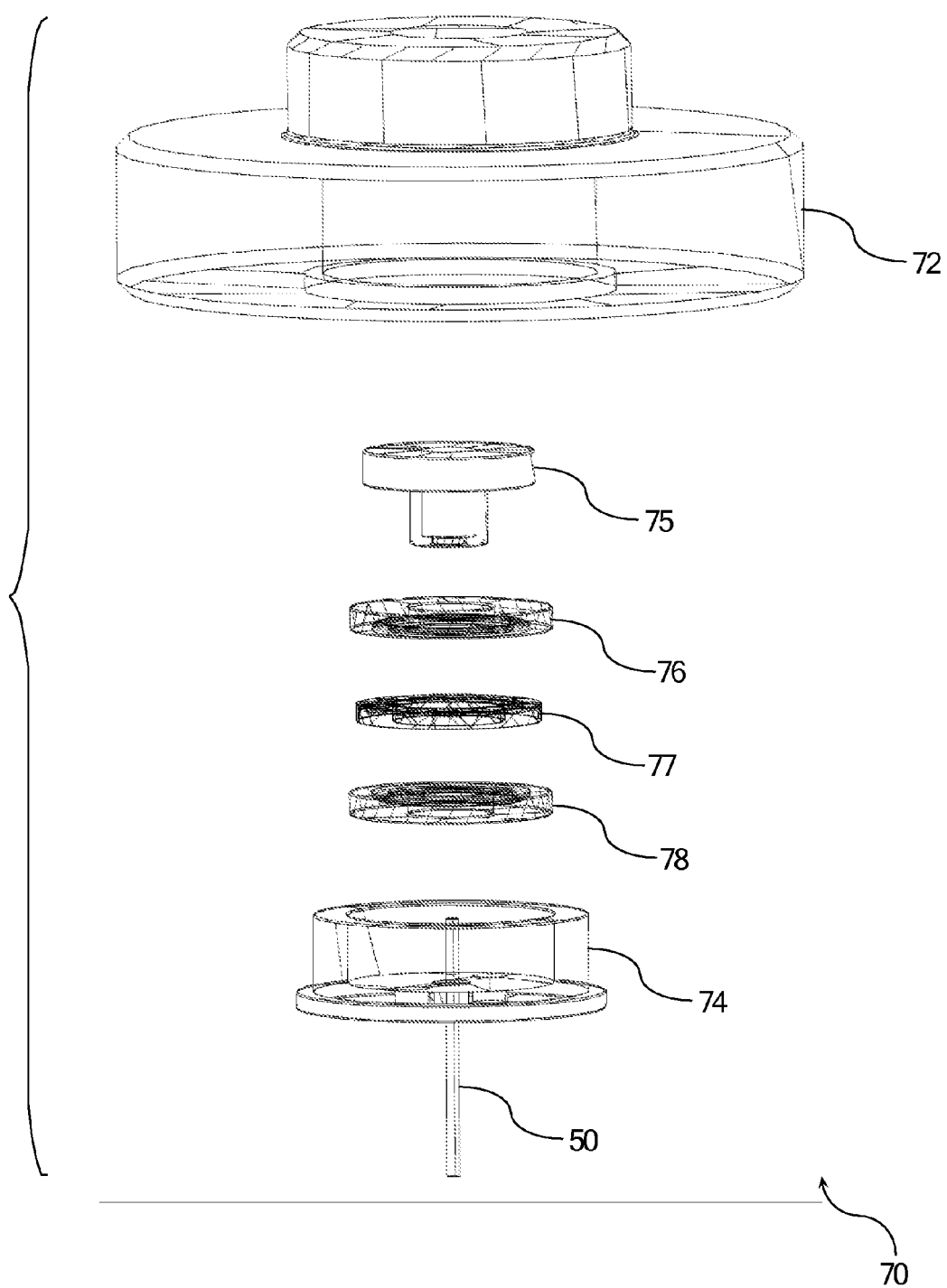
FIG. 6 is an exploded view of the thrust bearing subassembly illustrated in FIG. 5.

As is noted above, the tension control assembly 30 comprises a thrust bearing subassembly 70 that is secured to opposing ends of the tensile cord 50 and a solenoid plunger 34 of the tension control assembly 30. Referring to FIG. 6, the thrust bearing subassembly 70 comprises a thumb screw 72 and screw stop 74 that are configured for selective coupling and decoupling of the tensile cord 50 to the tension control assembly 30. The thrust bearing assembly further comprises a sleeve stop 75, a thrust plate 76, a bearing race 77, and a thrust plate 78. Generally, the thrust bearing subassembly 70 secures the end portion of the tensile cord 50 and permit translation of the tensile cord 50 from the relatively taut state, when a tension control mechanism 32 of the tension control assembly 30 is deactivated, to a relatively relaxed state, when the tension control mechanism 32 is activated.

It is noted that recitations herein of a component of the present invention being "configured" in a particular way, "configured" to embody a particular property or function in a particular manner, are structural recitations as opposed to recitations of intended use. More specifically, the references herein to the manner in which a component is "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present invention or to emphasize alternative or additional features that may or may not be utilized in a particular embodiment of the present invention.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A microscope comprising a microscope assembly and a lens positioner, wherein:
   the lens positioner comprises a tension control assembly, an adjustable lens extension assembly, and a tensile cord coupling the tension control assembly to the adjustable lens extension assembly;
   the tension control assembly is configured to control the degree of tension in the tensile cord;
   the adjustable lens extension assembly comprises a flexible linkage subassembly and a lens support subassembly;
   the flexible linkage subassembly comprises a proximal end and a distal end and is configured such that the distal end is movable relative to the proximal end through a plurality of degrees of freedom of movement;
   the lens support subassembly is secured to the distal end of the flexible linkage subassembly; and
   the flexible linkage subassembly is further configured such that the ease at which its distal end moves relative to its proximal end is a function of the degree of tension in the tensile cord, as controlled by the tension control assembly.

2. A microscope as claimed in claim 1 wherein the flexible linkage subassembly comprises a plurality of ball-and-socket type links, each comprising a central bore sufficient to accommodate passage of the tensile cord.

3. A microscope as claimed in claim 1 wherein the flexible linkage subassembly is configured to exhibit a mechanical preference for immobility of the distal end over mobility of the distal end as the degree of tension in the tensile cord increases.

4. A microscope as claimed in claim 1 wherein the flexible linkage subassembly comprises an adjustment arm configured to selectively adjust a degree of tension in the tensile cord by reducing or extending the length of the flexible linkage subassembly.

5. A microscope as claimed in claim 4 wherein the adjustment arm is configured to selectively adjust a degree of tension in the tensile cord via a threaded engagement.

6. A microscope as claimed in claim 1 wherein the flexible linkage subassembly comprises a cord accommodating passage extending from the proximal end of the flexible linkage subassembly to the distal end of the flexible linkage subassembly.

7. A microscope as claimed in claim 6 wherein the flexible linkage subassembly comprises a cord anchor at the distal end of thereof.

8. A microscope as claimed in claim 1 wherein the lens support subassembly is secured to the distal end of the flexible linkage subassembly via a magnetic coupling.

9. A microscope as claimed in claim 8 wherein the degree of securement attributable to the magnetic coupling is such that the lens support subassembly may be manually removed from the flexible linkage subassembly.

10. A microscope as claimed in claim 1 wherein the tension control assembly comprises a solenoid actuated tension control mechanism coupled to the tensile cord.

11. A microscope as claimed in claim 10 wherein the solenoid actuated tension control mechanism places the tensile cord in a relatively taut state when the solenoid is deactivated and in a relatively relaxed state when the solenoid is activated.

12. A microscope as claimed in claim 1 wherein the tension control assembly comprises a spring-loaded tension control mechanism that places the tensile cord in a relatively taut state when the tension control assembly is at rest.

13. A microscope as claimed in claim 1 wherein the tension control assembly comprises a controller and a foot-activated switch coupled to the controller.

14. A microscope as claimed in claim 1 wherein the tension control assembly comprises a controller and a touch-sensitive switching circuitry coupled to the controller.

15. A microscope as claimed in claim 14 wherein the touch-sensitive switching circuitry is configured to provide an electrical switching response to human contact with selected portions of the flexible linkage subassembly, the lens support subassembly, the lens housing subassembly, or combinations thereof.

16. A microscope as claimed in claim 1 wherein:
the tension control assembly comprises a mechanical stop;
the adjustable lens extension assembly is directly or indirectly anchored to the mechanical stop;
the mechanical stop is secured to the remainder of the tension control assembly via a magnetic coupling; and
the degree of securement attributable to the magnetic coupling is such that the mechanical stop may be manually removed from the flexible linkage subassembly.

17. A microscope as claimed in claim 1 wherein the tension control assembly comprises a thrust bearing subassembly configured to couple the tensile cord to the tension control assembly.

18. A microscope as claimed in claim 17 wherein the thrust bearing subassembly comprises a thumb screw and screw stop configured for selective coupling and decoupling of the tensile cord to the tension control assembly.

19. A microscope as claimed in claim 1 wherein the tension control assembly comprises a thrust bearing subassembly configured to secure an end portion of the tensile cord and permit translation of the tensile cord from a relatively taut state when a tension control mechanism of the tension control assembly is deactivated to a relatively relaxed state when the tension control mechanism of the tension control assembly is activated.

20. An ophthalmic microscope comprising a microscope assembly and a lens positioner, wherein:
the lens positioner comprises a tension control assembly, an adjustable lens extension assembly, and a tensile cord coupling the tension control assembly to the adjustable lens extension assembly;
the tension control assembly is configured to control the degree of tension in the tensile cord and comprises a solenoid actuated tension control mechanism coupled to the tensile cord;
the solenoid actuated tension control mechanism places the tensile cord in a relatively taut state when the solenoid is deactivated and in a relatively relaxed state when the solenoid is activated;
the tension control assembly comprises a controller and a foot-activated switch coupled to the controller or touch-sensitive switching circuitry coupled to the controller;
the adjustable lens extension assembly comprises a flexible linkage subassembly and a lens support subassembly;
the flexible linkage subassembly comprises a proximal end and a distal end and is configured such that the distal end is movable relative to the proximal end through a plurality of degrees of freedom of movement;
the flexible linkage subassembly comprises a cord accommodating passage extending from the proximal end of the flexible linkage subassembly to the distal end of the flexible linkage subassembly;
the flexible linkage subassembly is configured to exhibit a mechanical preference for immobility of the distal end over mobility of the distal end as the degree of tension in the tensile cord increases;
the lens support subassembly is secured to the distal end of the flexible linkage subassembly;
the flexible linkage subassembly is further configured such that the ease at which its distal end moves relative to its proximal end is a function of the degree of tension in the tensile cord, as controlled by the tension control assembly.

* * * * *